(12) United States Patent
Meir et al.

(10) Patent No.: US 7,965,833 B2
(45) Date of Patent: Jun. 21, 2011

(54) FEBRILE CONVULSION ALARM

(76) Inventors: Ronen Meir, Ashkelon (IL); Izak Rozin, West Bloomfield, MI (US)

( * ) Notice: Subject to any disclaimer, the term of this patent is extended or adjusted under 35 U.S.C. 154(b) by 1130 days.

(21) Appl. No.: 11/621,135

(22) Filed: Jan. 9, 2007

(65) Prior Publication Data

US 2008/0167583 A1 Jul. 10, 2008

(51) Int. Cl.
*H04M 1/65* (2006.01)
*A61B 5/11* (2006.01)

(52) U.S. Cl. .................. 379/387.01; 600/300; 600/549; 600/595

(58) Field of Classification Search ............. 318/400.21; 324/207.25; 327/72; 340/522, 567, 635; 348/219.1, 484, 700; 379/387.01; 600/595, 600/300, 549
See application file for complete search history.

(56) References Cited

U.S. PATENT DOCUMENTS

| | | | | |
|---|---|---|---|---|
| 4,625,199 A * | 11/1986 | Pantus | | 340/522 |
| 4,902,887 A * | 2/1990 | Everett, Jr. | | 250/221 |
| 4,943,712 A * | 7/1990 | Wilder | | 250/221 |
| 5,212,551 A * | 5/1993 | Conanan | | 348/484 |
| 5,309,147 A * | 5/1994 | Lee et al. | | 340/567 |
| 5,394,035 A * | 2/1995 | Elwell | | 327/72 |
| 5,889,469 A * | 3/1999 | Mykytiuk et al. | | 340/635 |
| 5,898,459 A * | 4/1999 | Smith et al. | | 348/219.1 |
| 5,964,720 A * | 10/1999 | Pelz | | 600/595 |
| 6,458,087 B1 * | 10/2002 | Al-Rasheed | | 600/549 |
| 6,641,544 B2 * | 11/2003 | Liu | | 600/549 |
| 6,859,237 B2 * | 2/2005 | Swartz | | 348/700 |
| 6,917,172 B2 * | 7/2005 | Brenden et al. | | 318/400.21 |
| 7,396,331 B2 * | 7/2008 | Mack et al. | | 600/300 |
| 7,696,746 B2 * | 4/2010 | Shimomura et al. | | 324/207.25 |
| 2003/0230721 A1 * | 12/2003 | Lee | | 250/342 |

* cited by examiner

*Primary Examiner* — Gerald Gauthier
(74) *Attorney, Agent, or Firm* — Deborah Gador

(57) ABSTRACT

A device and method for detecting febrile convulsions, the device including a detector for detecting motion of the device and providing an output corresponding thereto, a capacitor coupled to the detector and charged by the output of the detector, a resistor coupled to the capacitor to provide discharge of the capacitor, a comparator for comparing a voltage level of the capacitor to a reference voltage and providing a signal when the voltage level of the capacitor is greater than the reference voltage, and an indicator driven by the signal from the comparator to provide an indication of febrile convulsions.

9 Claims, 4 Drawing Sheets

FIG 3A  C4 CHARGE

X=COMPARATOR TRIGER LEVEL

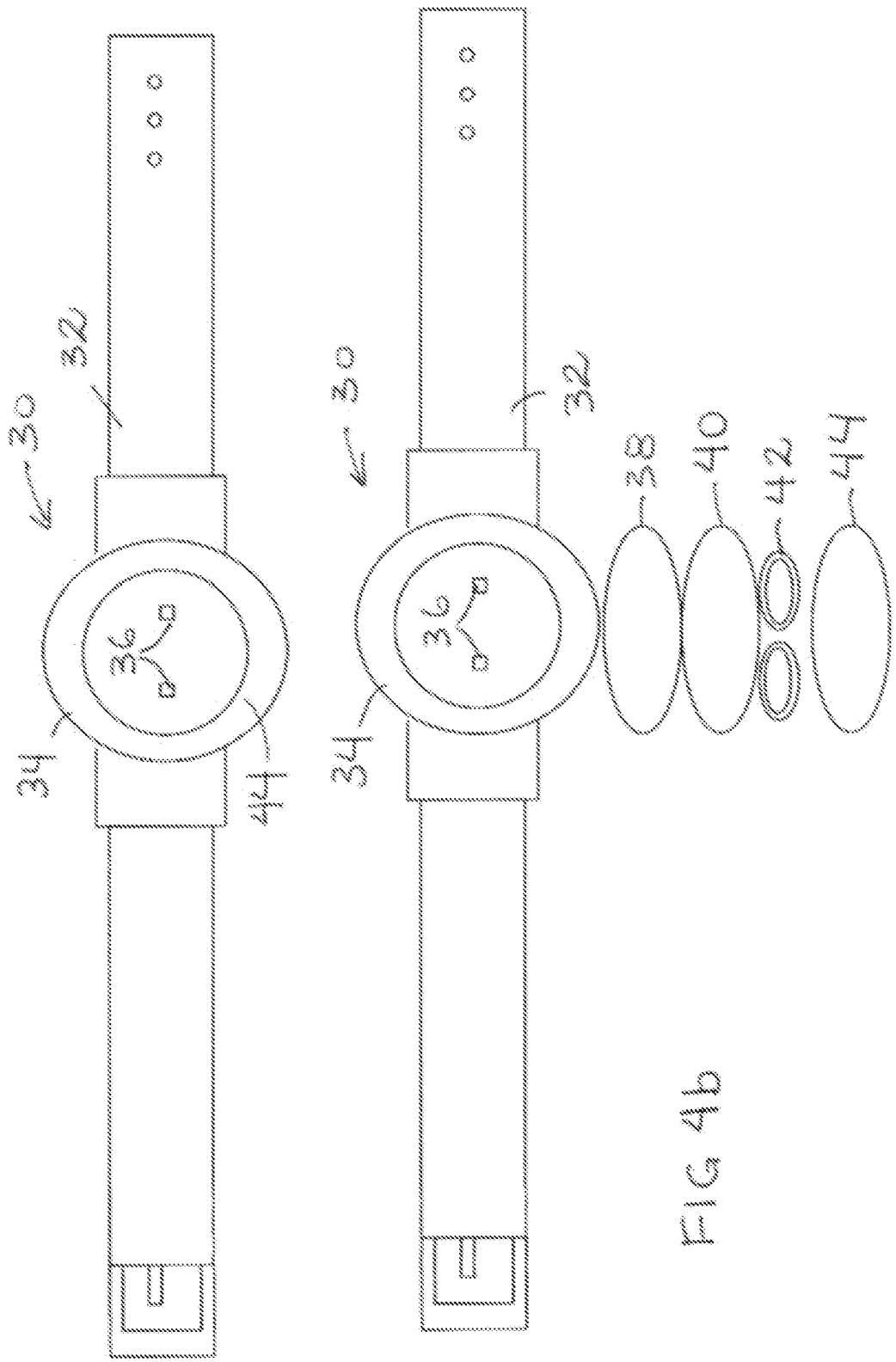

FEBRILE CONVULSION ALARM

FIELD OF THE INVENTION

The present invention relates to a device and method for detecting the occurrence of febrile convulsion or epileptic seizure and alerting the parents or other caregivers of such event, especially during sleep.

BACKGROUND OF THE INVENTION

Parent so children who are susceptible to such events (convulsions or seizures) suffer from stress, anxiety and lack of sleep, due to their continuing fear that the event may take place at such time as they are unaware of the event and unable to take care of the child. The device of the present invention will enable thee concerns to be overcome, by ensuring that the parents and caregivers are made aware of the event as soon as it commences. At present, there are known devices for notifying a caregiver when an infant stops breathing or when there is a significant rise in skin temperature, but the only way a parent is aware of convulsions is if he or she happens to be beside the child when they occur.

Febrile convulsions are characterized by frequent violent movement of the sufferer's hands and/or legs. Febrile convulsions occur in young children when there is a rapid increase in their body temperatures. They affect up to 5% of children between the ages of one and four, but can affect children between six months and about five years old.

Children who are at risk may naturally have a lower resistance to febrile convulsion than others. Children may inherit the tendency to suffer febrile convulsions from their parents. If either parent suffered a febrile convulsion as a child, the risk of the child having one or more rises 10 to 20%. If both parents and their child have at some point suffered a febrile convulsion, the risk of another child having one rises 20 to 30%.

Nevertheless, the child's susceptibility also depends on whether the child frequently gets infections. About 40% of children who have had febrile convulsions will get them again at some stage, although the risk differs greatly from child to child. The child's risk of febrile convulsions rises if:
 they are genetically predisposed to it
 they suffer from frequent illnesses, particularly those which cause high temperatures (fever)
 the first attack of febrile convulsion was accompanied by a relatively low body temperature—below 39° C.

One in a thousand children may suffer a febrile convulsion after receiving the MMR (measles, mumps, rubella) vaccine. In these cases, it occurs 8 to 10 days after the vaccination and is caused by the measles component of the vaccine. However, this causes only about one tenth of cases of febrile convulsion compared with measles itself.

The symptoms of febrile convulsions are:
 The attack often begins with the child losing consciousness, and shortly afterwards the body, legs and arms go stiff.
 The head is thrown backwards and the arms and legs begin to jerk.
 The skin goes pale and may even turn blue, briefly.
 The attack ends after a few minutes, and the shaking stops. The child goes limp, and then normal colour and consciousness slowly return.
 Some children regain consciousness faster than others.
 Caregivers should not intervene while the attack is taking place, except in the circumstance outlined below.
 Carefully turn the child's head to one side to prevent choking. In the past, it was common to place a stick in the child's mouth to prevent bites to the tongue or lips.
 When the fit subsides, the child should be kept in the recovery position on his on her side. If fits are prolonged or follow each other rapidly, an ambulance should be called.

The first time a child suffers febrile convulsions, he should be admitted to hospital. If the child has suffered attacks on earlier occasions, hospitalization is not always necessary. However, it is always important, for example, to determine whether the convulsions are only due to a harmless viral infection. For this reason, a doctor should always be consulted following an attack.

If the child has a history of febrile convulsions, parents are sometimes advised to have the medicine diazepam ready in case an attack takes place. It can be given into the rectum from a specific rectal tube and takes effect in a few minutes.

If the attack goes on for more than five minutes treatment can be repeated, but medical advice should always be sought in any prolonged fit. Dosage instructions must be carefully adhered to.

Care should be taken to ensure the child is not too hot, by removing extra clothing or bedclothes.

Some doctors advise parents to give the child mild painkillers, such as paracetamol (e.g., Calpol) or ibuprofen (e.g., Nurofen for children). This lowers the temperature by between 1 and 1.5° C. It is important to give the recommended dose, only.

Although febrile convulsions look like epileptic fits, they rarely have anything in common with this illness. 99% of children who have had a febrile convulsion have no more fits after they reach school age.

Although febrile convulsion often seems frightening, it rarely results in any permanent injuries. If, however, the convulsions last a long time or the child suffers several attacks in quick succession, slight disturbances in the brain function may occur.

Temperature-lowering medicines, such as paracetamol, can help lower body temperature but need to be repeated. If not, the temperature will rise rapidly again.

Accordingly, there is a long felt need for a device for providing a warning to parents or caregivers when a febrile convulsion begins, and it would be very desirable is such a device were of small size for wearing on the arm or leg of a child.

SUMMARY OF THE INVENTION

The present invention relates to a device for providing an indication of the onset of a febrile convulsion. The device is able to distinguish between such movements and the type of movements which routinely take place during sleep.

According to a preferred embodiment of the invention, the device is configured in a device to be worn by the patient, similar to a wrist watch, around the wrist or ankle.

There is provided according to the present invention a device for detecting febrile convulsions, the device including a detector for detecting motion of the device and providing an output corresponding thereto, a capacitor coupled to the detector and charged by the output of the detector, a resistor coupled to the capacitor to provide discharge of the capacitor, a comparator for comparing a voltage level of the capacitor to a reference voltage and providing a signal when the voltage level of the capacitor is greater than the reference voltage, and an indicator driven by the signal from the comparator to provide an indication of febrile convulsions.

According to a preferred embodiment of the invention, the device includes device for detecting febrile convulsions, the device including a tilt movement sensor for detecting motion of the device and providing an output signal corresponding thereto; an input network for providing the output signal to a mono-stable pulse detector; a capacitor coupled to the detector and charged by the output of the detector; a resistor coupled to the capacitor to provide discharge of the capacitor; a signal alarm level comparator for comparing a voltage level of the capacitor to a reference voltage and providing a signal when the voltage level of the capacitor is greater than the reference voltage; a piezo buzzer driven by the signal from the comparator via an audio oscillator to provide an indication of febrile convulsions; a small coin-type Lithium battery for providing battery power; a battery level comparator to provide an indication of low battery power; an LED for indicating system operation; and an LED for indicating low battery power.

There is also provided according to the invention method of detecting febrile convulsions, the method including detecting motion of a device and providing an output signal corresponding thereto; charging a capacitor coupled to the detector by the output of the detector; providing discharge of the capacitor by a resistor coupled to the capacitor; comparing a voltage level of the capacitor to a reference voltage and providing a signal when the voltage level of the capacitor is greater than the reference voltage; and providing an indication of febrile convulsions by means of an indicator driven by the signal from the comparator.

BRIEF DESCRIPTION OF THE DRAWINGS

The present invention will be further understood and appreciated from the following detailed description taken in conjunction with the drawings in which:

FIG. 3c is a graph illustrating charge and discharge over time of the capacitor of FIG. 3a; and FIGS. 4a and 4b are respective plan and exploded views of a device according to the invention in the form of a wrist watch.

DETAILED DESCRIPTION OF THE INVENTION

The invention described herein is a device for detecting the occurrence of febrile convulsions or epileptic seizures and alerting the parents or other caregivers of such event, especially during sleep.

Figure 1:
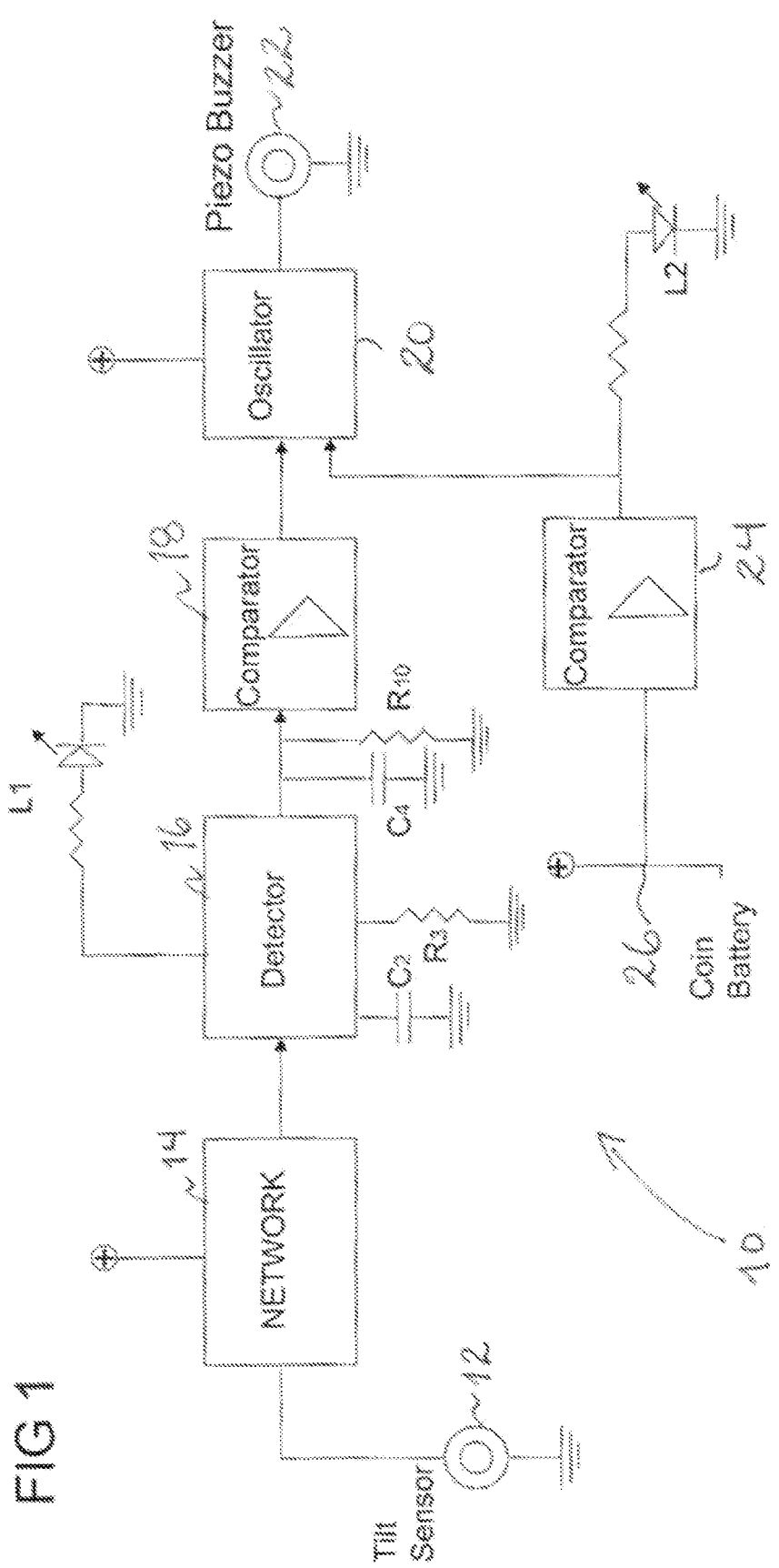
FIG. 1 is a block diagram illustration of a device for providing an indication of febrile convulsions constructed and operative in accordance with one embodiment of the present invention.

Referring to FIG. 1, there is shown a block diagram illustration of a device 10 for providing an indication of febrile convulsions, constructed and operative in accordance with one embodiment of the present invention. Device 10 includes a detector or movement sensor, preferably a tilt sensor 12, which detects movement and sends electrical signals to the on/off form (opens or closes a circuit) to a filter network 14. Filter network 14 adapts the signal from the filter network to a CMOS mono-stable pulse detector 16, such as TS555, which, in turn, charges a capacitor C4 for a pre-set duration.

The capacitor C4, therefore, is charged with every movement of device 10. When there is no movement, the capacitor C4 is discharged by a resistor R10 connected in parallel to the capacitor. Capacitor C4 and resistor R10 are coupled to the input of a comparator 18. Comparator 18 has a pre-selected trip point at which it provides an output signal (virtual ground) to power an oscillator 20. Non-rapid movement allows the capacitor to discharge in the time between movements and therefore the charge does not approach the trip point of comparator 18. In contrast, rapid movement causes recharging of capacitor C4, up to the trip point.

The voltage across the capacitor enters the CMOS comparator and is compared to a pre set reference voltage. When the voltage of the capacitor becomes higher than the voltage of the reference resistor, the comparator provides power to a CMOS oscillator 20 that generates an audible frequency signal, which activates a buzzer 22. Buzzer 22 may be a piezo buzzer, or any other suitable indicator device.

In addition, a second comparator 24 works in inverting mode, measures the voltage of the battery 26 or batteries powering the device, and when the voltage falls below a pre-set level that shows that the power is exhausted and the device is unable to power a convulsion alarm, the comparator provides an output signal and drives the oscillator 20 to sound a continuous alarm and/or an LED L2 to provide a lighting alert, to tell the user to replace or recharge the batteries.

A second LED L1 monitors the output of the detector and lights up whenever the detector detects movement. This shown that the detector works effectively.

The device an be tested effectively by shaking it rapidly until the alarm is sounded. It will be appreciated that, instead of an oscillator and buzzer, any alternative means of providing an audible or visual indication of convulsions can be utilized. If desired, a transmitter can be activated to send a warning signal to a receiving device.

Figure 2:
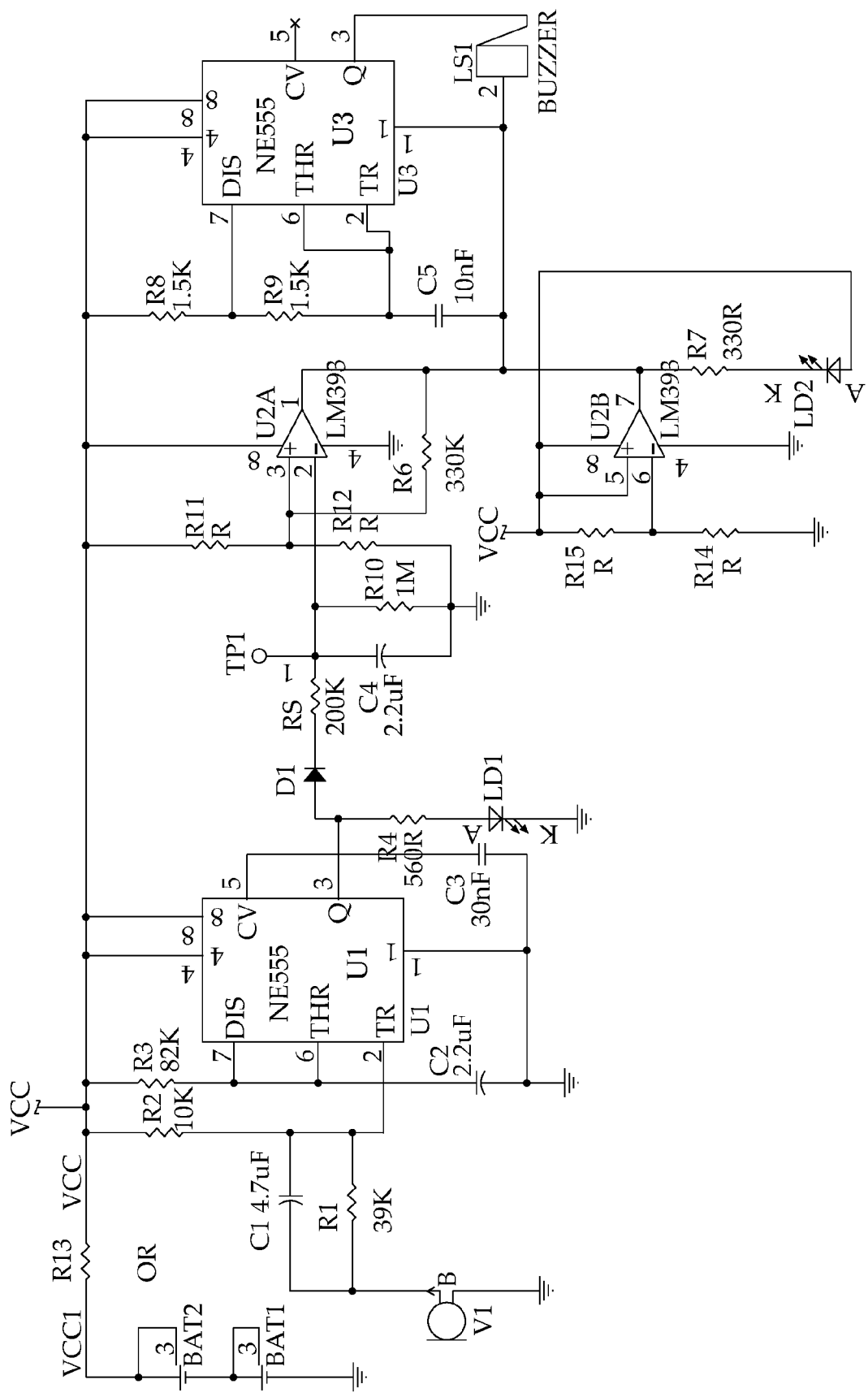
FIG. 2 is a schematic diagram of the electronics of a device according to one embodiment of the invention.

FIG. 2 is a schematic diagram of the electronics of a device according to one embodiment of the invention, similar to that shown in FIG. 1. As seen in FIG. 2, a tilt sensor V1 is connected to a filter network consisting of a resistor R1 and a capacitor C1, and resistor R2 is connected to U1, a CMOS mono-stable timer, at the trigger pin 2. Signals from sensor V1 trigger the mono-stable timer U1 to produce pulses whose duration is set by resistor R3 and capacitor C2.

The pulses are actually expanded in time and produce the output at pin 3 of U1. Pin 3 is connected to LD1 to show pulses detected. The signal from U1 Pin 3 is delivered via diode D1 and resistor R5 to a network of capacitor C4 and resistor R10 that is connected to the capacitor C4 in parallel.

C4 charges every time it accepts charges from U1, and R10 discharges the pulses at a slow rate. D1 blocks C2 charge from discharge via LD1. It will be appreciated that changing the value of capacitor C4 and resistor R10, and possibly of resistor R3 and capacitor C2, permits one to define the sensitivity level of the device.

Instead of a resistor R13 which is 0 Ohm, a miniature power switch may be provided to turn the power on and off in the circuit, so as to save the battery when the device is not in use.

Figure 3:
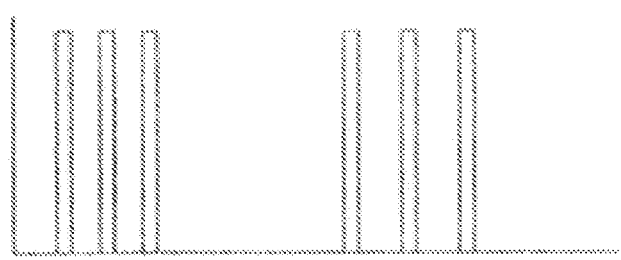
FIGS. 3a, 3b, 3c are schematic graphs illustrating charge of the charge capacitor at the input of the comparator in a device according to one embodiment of the invention.
FIG. 3d is a graph illustrating output pulses from the detector during movement of the tilt sensor.
Figure 3E:
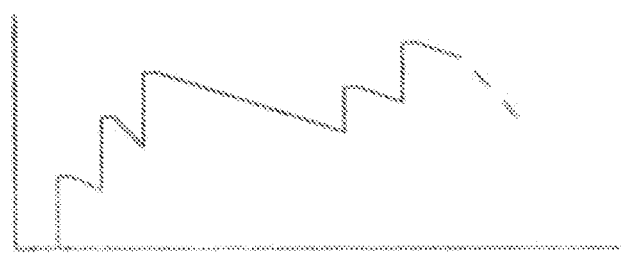
Figure 3B:
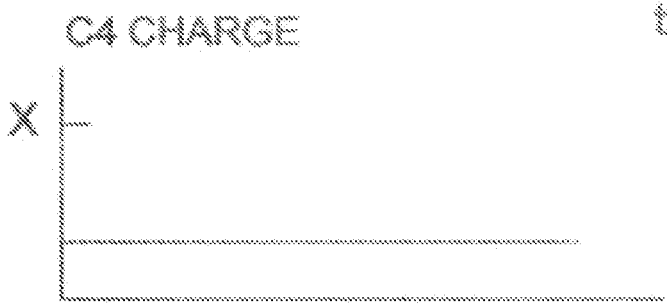
Figure 3B:
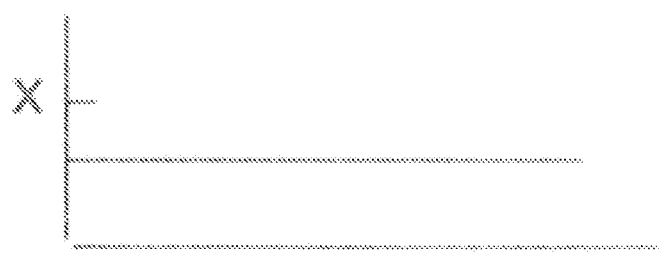
Figure 3C:
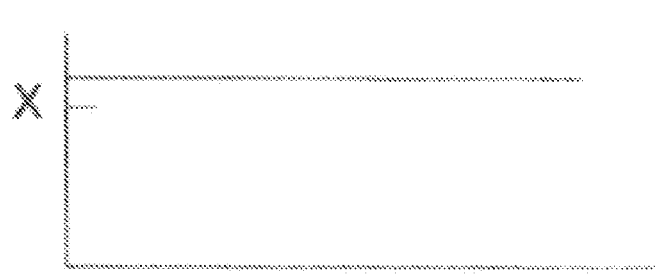

In the event of rapid pulses coming from Pin 3, as shown in FIG. 3D, capacitor C4 will charge more and more, as illustrated in FIGS. 3a, 3b, 3c, until it passes the trigger point of comparator U2A, shown at reference numeral X. The charge and discharge of capacitor C4 is illustrated graphically in FIG. 3e. When the charge passes the trigger point at the input of the comparator U2A, which can be measured at test point TP1, the level of charge of capacitor C4 enters into comparator U2A Pin 2 where it is compared to the voltage level of the comparator U2A at Pin 3 set by R11 and R12 resistor network voltage divider. When the voltage at Pin 2 is higher than the reference voltage at Pin 3, comparator U2A provides a virtual ground to close the circuit and actuate oscillator U3.

The values of resistors R12 and R11 set the level at which comparator U2A will trigger the output to cause sounding of an alarm.

When a series of pulses come from the movement of the detector via U1, D1, R5 and charge C4 to the level that U2A triggers an output, this output becomes low and provides ground connection to close the circuit to activate U3 CMOS TS555 multi-vibrator that oscillates in a frequency set by R8, R9 and C5.

The output of U3 at Pin 3 is fed to a buzzer LS1, or other warning device, and closes the circuit with the ground provided by U2A Pin 1, which activates the sound alarm.

When the series of pulses that charge C4 ceases, i.e., there is no longer movement of the device, C4 discharges via R10 and comparator U2A Pin 1 goes high which, in turn, deactivates U3 and terminates the alarm.

In case of several pulses with long intervals between them (to be set by C2, C4 and R10) capacitor C4 charges and discharges reaching the trigger of U2A and, therefore, the alarm stays off. This corresponds to regular slow movement during sleep.

Integrated circuit U2B is a comparator that compares the battery level from VCC at Pin 6 via R15 and R14 voltage dividers to provide an alarm in case of low battery via Pin 7. When Pin 7 goes low, LD2 lights up to signal low battery. In addition, U3 is activated to provide a buzzer sound. The user will know that the problem is a low battery and not the advent of convulsion.

All components preferably are incorporated in a miniature circuit, configured to be fitted inside a wrist watch type casing which can be worn by the patient, either on the wrist or ankle, very conveniently and without disturbance. The entire circuit is preferably built on a small printed circuit board, that could be fitted into a wrist watch or other similar small attachment, suitable for the hand or leg of a child. One example of a suitable structure is shown in FIGS. 4a and 4b, respective plan and exploded views of a device according to the invention in the form of a wrist watch 30. Watch 30 includes a watch strap 32 on which a watch body 34 is mounted. Two LED's 36 are mounted in the body 34. A piezo buzzer 38, printed circuit board 40 with batteries 42, are provided on the body and closed with a cover 44. Batteries 42 can be, for example coin type Li batteries, such as CR1220. Alternatively, batteries 42 can be one or more small rechargeable batteries with a socket (not shown) in body 34 for a charger.

The circuit of the invention can be embodies in a Printed Circuit Board (PCB). Alternatively, the circuit can built into an ASIC or microprocessor to facilitate further miniaturization.

It will be appreciated that, in certain cases, such as epilepsy and other complex illnesses, the child may only move one hand, rather than both hands, during a convulsion. In such cases, it is preferable to utilize two devices according to the invention, one on each hand, which act independently of one another, to ensure activation of a timely warning signal.

While the invention has been described with respect to a limited number of embodiments, it will be appreciated that many variations, modifications and other applications of the invention may be made. It will further be appreciated that the invention is not limited to what has been described herein-above merely by way of example. Rather, the invention is limited solely by the claims which follows.

The invention claimed is:

1. A device for detecting febrile convulsions, the device comprising:
    a tilt movement sensor and a mono-stable pulse detector for detecting motion of the device and providing an output signal corresponding thereto;
    a capacitor coupled to said detector and charged by the output of said detector;
    a resistor coupled to said capacitor to provide discharge of said capacitor;
    a comparator for comparing a voltage level of said capacitor to a reference voltage and providing a signal when said voltage level of said capacitor is greater than said reference voltage;
    an indicator driven by said signal from said comparator to provide an indication of febrile convulsions; and
    a strap adapted and configured to be worn on a baby's body, said detector, capacitor, resistor, comparator and indicator being mounted on said strap.

2. The device according to claim 1, wherein said indicator is a buzzer, and said signal from said comparator powers an oscillator for actuating said buzzer.

3. The device according to claim 1, further comprising a battery monitor for indicating low battery power.

4. The device according to claim 1, wherein said strap is adapted and configured to be worn on a baby's hand.

5. The device according to claim 1, wherein said detector, capacitor, resistor, comparator and indicator are embodied in an ASIC.

6. The device according to claim 1, wherein said detector, capacitor, resistor, comparator and indicator are embodied in a Printed Circuit Board (PCB).

7. The device according to claim 1, wherein said detector, capacitor, resistor, comparator and indicator are emulated by a microprocessor.

8. A device for detecting febrile convulsions, the device comprising:
    a tilt movement sensor for detecting motion of the device and providing an output signal corresponding thereto;
    an input filter network for providing said output signal to a mono-stable pulse detector;
    a capacitor coupled to said detector and charged by the output of said detector;
    a resistor coupled to said capacitor to provide discharge of said capacitor;
    a signal alarm level comparator for comparing a voltage level of said capacitor to a reference voltage and providing a signal when said voltage level of said capacitor is greater than said reference voltage;
    a piezo buzzer driven by said signal from said comparator via an audio oscillator to provide an indication of febrile convulsions;
    a small coin-type Lithium battery for providing battery power;
    a battery level comparator to provide an indication of low battery power;
    an LED for indicating system operation; and
    an LED for indicating low battery power.

9. A method of detecting febrile convulsions, the method comprising:
    mounting a tilt movement sensor and a mono-stable pulse detector in a strap of a device adapted to be worn on a baby's body;

detecting tilting motion of a device by means of said tilt movement sensor and said mono-stable pulse detector and providing an output signal corresponding thereto;

charging a capacitor in said strap coupled to said detector by the output of said detector;

providing discharge of said capacitor by a resistor in said strap coupled to said capacitor;

comparing a voltage level of said capacitor to a reference voltage and providing a signal when said voltage level of said capacitor is greater than said reference voltage; and providing an indication of febrile convulsions by means of an indicator driven by said signal from said comparator.

\* \* \* \* \*